United States Patent [19]

Morgan, Jr. et al.

[11] Patent Number: 4,920,116
[45] Date of Patent: Apr. 24, 1990

[54] N-(AMINOALKYL)-SUBSTITUTED(N OR C ALKYL)-ARYL-4(METHYLSULFONYLAMINO)BENZAMIDES

[75] Inventors: Thomas K. Morgan, Jr., Morris Plains, N.J.; Klaus Nickisch, West Berlin, Fed. Rep. of Germany

[73] Assignee: Schering A.G., Berlin, Fed. Rep. of Germany

[21] Appl. No.: 283,712

[22] Filed: Dec. 13, 1988

Related U.S. Application Data

[63] Continuation-in-part of Ser. No. 914,216, Oct. 2, 1986, abandoned.

[51] Int. Cl.$^5$ ............................................. C07C 143/74
[52] U.S. Cl. ..................... 514/210; 514/212; 514/218; 514/237.8; 544/58.1; 544/58.2; 546/244; 548/538; 564/80; 564/83; 564/86; 564/90; 564/91; 564/99
[58] Field of Search ................. 564/99, 80, 83, 86, 564/90, 91; 514/210, 212, 218, 222, 223, 229; 544/58.1, 58.2; 546/244; 548/539

[56] References Cited

U.S. PATENT DOCUMENTS

| | | | |
|---|---|---|---|
| 3,341,584 | 9/1967 | Larsen et al. | 564/99 X |
| 4,044,150 | 8/1977 | Kreighbaum et al. | 564/99 X |
| 4,404,224 | 9/1983 | Asato | 564/99 X |
| 4,544,654 | 10/1985 | Davey et al. | 564/210 |
| 4,545,995 | 10/1985 | Lumma et al. | 564/99 X |
| 4,629,739 | 12/1986 | Davey et al. | 564/99 X |

FOREIGN PATENT DOCUMENTS 364248  10/1962  Switzerland ..................... 564/99

Primary Examiner—Floyd D. Higel
Attorney, Agent, or Firm—Elizabeth A. Bellamy; John L. White; I. William Millen

[57] ABSTRACT

N-(aminoalkyl)-substituted(N or C alkyl)-aryl-4-(methylsylfonylamino)benzamides of the formula

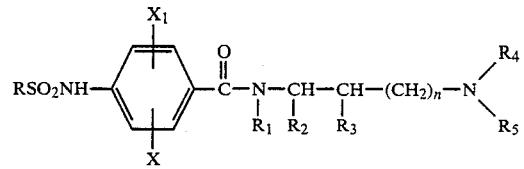

wherein R is $C_1$–$C_4$ straight chain alkyl, one of $R_1$, $R_2$ and $R_3$ is a phenyl or naphthyl group and the others are hydrogen, —$NR_4R_5$ is a secondary or teritary amino group, X and $X_1$ are hydrogen or alkyl and n is 0 or 1, are useful as antiarrhythmic agents in the treatment of cardiac arrhythmias especially as combination Class I/Class III agents.

24 Claims, No Drawings

N-(AMINOALKYL)-SUBSTITUTED(N OR C ALKYL)-ARYL-4(METHYLSULFONYLAMINO)-BENZAMIDES

CROSS REFERENCE TO RELATED APPLICATIONS

This Application is a continuation-in-part of application Ser. No. 914,216 filed October 2, 1986, now abandoned.

PRIOR ART

The compounds described herein provide antiarrhythmic efficacy by the slowing of conduction and by the prolonging of ventricular refractoriness in cardiac tissue. Thus these compounds exhibit Class I/III antiarrhythmic activity. These compounds have been compared to the known Class I agent flecainide, the Class III agent clofilium and the Class III agent sematilide—this latter compound is representative of the compounds of U.S. Pat. Nos. 4,544,654 and 4,629,739 which agents are also substituted sulfonamidobenzamides.

FIELD OF THE INVENTION

This invention relates to novel N-(aminoalkyl)-substituted(N or C alkyl)aryl-4(methylsulfonylamino)benzamides and their use as antiarrhythmic agents. Specifically, this invention relates to N-aminoalkyl-4-(sulfonamido)benzamides which are substituted by various aryl moieties and their pharmaceutically acceptable salts, to pharmaceutical compositions containing them as active ingredients and to the method of using them in the treatment of arrythmias more especially in the treatment of arrhythmias wherein a combination class I/- class III action is most effective.

GENERAL DESCRIPTION OF THE INVENTION

Composition-of-Matter Aspect

In its composition-of-matter aspect this invention relates to novel aryl substituted N-aminoalkyl-4-(sulfonamido)benzamides and their pharmaceutically acceptable salts. Particularly, this invention relates to the novel compounds defined by the following Formula I:

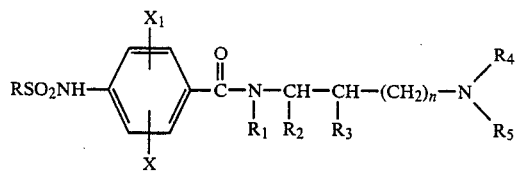

wherein R is a $C_1$–$C_4$ straight chain alkyl; $R_1$, $R_2$ and $R_3$ are hydrogen, phenyl, substituted phenyl, naphthalenyl and substituted naphthalenyl; $R_4$ and $R_5$ are hydrogen, $C_1$–$C_8$ straight or branched chain alkyl, allyl, cycloalkyl, cycloalkyl(lower)alkyl, phenyl(lower)alkyl, substituted phenyl(lower)alkyl or when taken together form a saturated heterocyclic ring of from 4 to 8 ring members which may optionally contain a —O— or

linkage; $R_6$ is hydrogen, $C_1$–$C_8$ straight or branched chain alkyl, phenyl and substituted phenyl; X and $X_1$ are the same or independently hydrogen or $C_1$–$C_4$ straight or branched chain alkyl; n is the integer 0 or 1. The invention is inclusive of the pharmaceutically acceptable salts and carries the provisos that:

(a) two of $R_1$, $R_2$ or $R_3$ must be hydrogen; and
(b) only one of $R_4$ and $R_5$ can be hydrogen.

As previously indicated, contemplated as part of this invention are the pharmaceutically acceptable salts of the compounds of Formula I. Useful acids for this purpose include both inorganic and organic acids such as hydrochloric, hydrobromic, sulfuric, phosphoric, acetic, propionic, benzoic, naphthoic, oxalic, succinic, maleic, malic, adipic, lactic, tartaric, citric, salicylic, methanesulfonic and p-toluenesulfonic acids.

It is to be understood that the definition of the compounds of Formula I encompasses all possible stereoisomers and mixtures thereof which possess the activity discussed below. In particular it encompasses racemic modifications and any optical isomers which possess the indicated activity.

In the above Formula I substituted phenyl and substituted naphthalenyl are taken to mean phenyl or naphthalenyl moieties which may be substituted with 1 to 3 substituents selected from the group consisting of $C_1$–$C_4$ alkyl, $C_1$–$C_4$ alkoxy, trifluoromethyl, fluorine, chlorine and bromine. The term allyl shall mean 2-propenyl. The term lower alkyl/alkoxy shall be taken to mean a straight or branched chain alkyl/alkoxy of from 1 to 4 carbon atoms. The term cycloalkyl shall refer to a saturated carbocycle of from 3 to 7 carbon atoms and a cycloalkyl(lower)alkyl shall contain from 4 to 11 carbon atoms.

When $R_4$ and $R_5$ together form a saturated heterocyclic ring of from 4 to 8 ring members which may optionally contain an —O— or

linkage, the following moieties are envisioned as being inclusive albeit not restricted thereto.

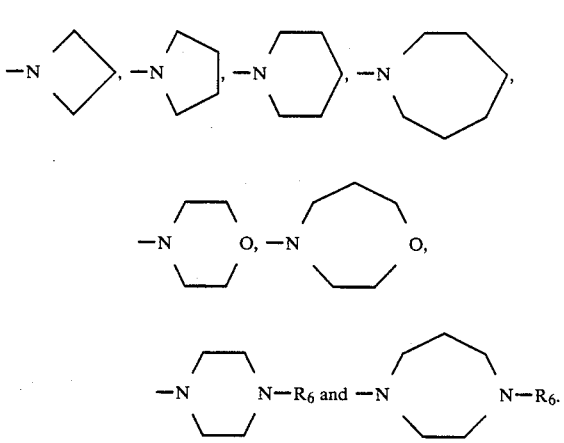

Preferred classes of compounds embodied by this invention are those of the above general Formula I having one of the following characteristics:

(a) where $R_2$ and $R_3$ are hydrogen;
(b) where $R_1$ and $R_3$ are hydrogen, and
(c) where $R_1$ and $R_2$ are hydrogen.

The more preferred compounds of this invention are those containing one of the above a–c characteristics and wherein:

(e) R is methyl,
(f) X and $X_1$ are hydrogen, and
(g) where n is 0.

The most preferred compounds are those having one of the a–c characteristics and all of the e, f, and g characteristics.

The compounds which follow are some of those which serve to exemplify various aspects of the invention described herein.

(1) N-[2-(Diethylamino)ethyl]-N-(2,6-dimethylphenyl)-4-[(methylsulfonyl)amino]benzamide.
(2) N-[2-(Diethylamino)ethyl]-4-[(methylsulfonyl)amino]-N-(phenyl)benzamide.
(3) N-[2-(Diethylamino)ethyl]-4-[(methylsulfonyl)amino]-N-(1-naphthalenyl)benzamide.
(4) N-[2-(Diethylamino)ethyl]-N-[2,6-bis(1-methylethyl)phenyl]-4-[(methylsulfonyl)amino]benzamide.
(5) 4-[(Butylsulfonyl)amino]-N-[3-chloro-4-methoxyphenyl]-N-[2-[ethyl(heptyl)amino]ethyl]benzamide.
(6) N-[2-Chloro-4-methoxyphenyl]-N-[2-[(2-propenyl)cyclohexylmethyl)amino]ethyl]-4-[(propylsulfonyl)amino]benzamide.
(7) N-[4-(1,1-Dimethylethyl)phenyl]-4-[(methylsulfonyl)amino]-N-[3-(4-morpholinyl)propyl]benzamide.
(8) N-[4-Butoxyphenyl]-N-[3-[(2-(3,4-dimethoxyphenyl)ethyl)(methyl)amino]propyl]-4-[(methylsulfonyl)amino]benzamide.
(9) N-[4-Bromophenyl]-4-[(methylsulfonyl)amino]-N-[2-[(2-phenylethyl)amino]ethyl]benzamide.
(10) N-[2-(Diethylamino)-1-(phenyl)ethyl]-4-[(methylsulfonyl)amino]benzamide.
(11) N-[2-(Diethylamino)-1-(naphthalen-1-yl)ethyl]-4-[(methylsulfonyl)amino]benzamide.
(12) N-[2-(Diethylamino)-2-(naphthalen-1-yl)ethyl]-4-[(methylsulfonyl)amino]benzamide.
(13) N-[2-(3,4-Dichlorophenyl)-3-(1-pyrrolidinyl)propyl]-4-[(methylsulfonyl)amino]benzamide.
(14) N-[3-(Dipropylamino)-2-(3,4,5-trimethoxyphenyl)propyl]-3-methyl-4-[(methylsulfonyl)amino]benzamide.
(15) N-[2-(2,6-Difluorophenyl)-3-(4-morpholinyl)propyl]-4-[(ethylsulfonyl)amino]benzamide.
(16) N-[2-(2-Naphthalenyl)-3-(4-pentylpiperazin-1-yl)propyl]-4-[(propylsulfonyl)amino]benzamide.
(17) N-[2-(2,4-Dichlorophenyl)-2-(piperidin-1-yl)ethyl]-4-[(methylsulfonyl)amino]benzamide.
(18) N-[2-[(Cyclohexylmethyl)amino]-2-(3,4,5-trimethoxyphenyl)ethyl]-4-[(ethylsulfonyl)amino]benzamide.
(19) N-[2-Diethylamino-1-(3,4,5-trimethoxyphenyl)ethyl]-4-[(methylsulfonyl)amino]benzamide.
(20) N-[1-(2,4-Dichlorophenyl)-2-(diethylamino)ethyl]-4-[(methylsulfonyl)amino]benzamide.
(21) 4-[(Ethylsulfonyl)amino]-N-[1-(4-methoxyphenyl)-2-(1-piperidinyl)ethyl]benzamide.
(22) N-[1-(2,4-Dichlorophenyl)-2-(bis(2-propenyl)amino)ethyl]-4-[(methylsulfonyl)amino]benzamide.
(23) N-[2-((Cyclohexylmethyl)amino)-1-(4-trifluoromethylphenyl)ethyl]-4-[(propylsulfonyl)amino]benzamide.

PROCESS ASPECT

In general, the compounds of this invention may be prepared by various reactants and processes known in the art. Illustrative but not limiting as the reactants and processes utilized for the preparation of the compounds of the invention are the following Schemes A, B, C & D. It is to be noted that where in Schemes A–D, anilines, acetophenones and phenylacetonitriles are shown as starting materials the corresponding naphthylamines, acetonaphthones and naphthylacetonitriles may also be employed.

SCHEME A

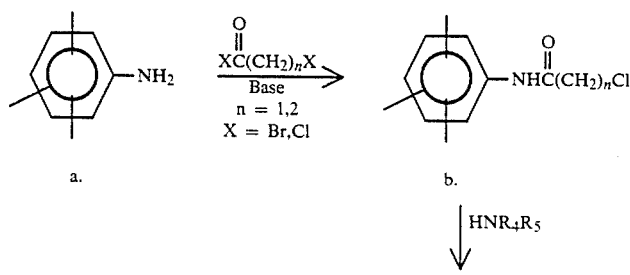

SCHEME A

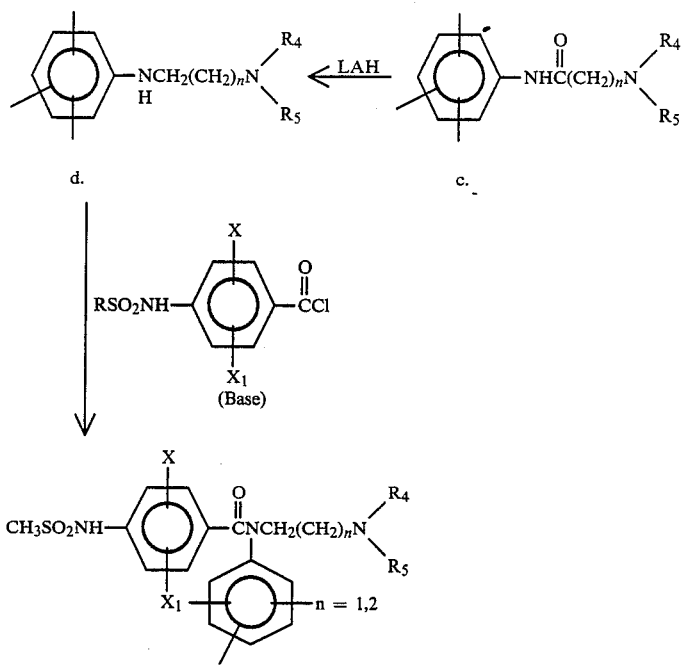

The route outlined in the foregoing Scheme A illustrates the preparation of the compounds of the invention wherein $R_1$ is aryl and $R_2$ and $R_3$ are hydrogen. An appropriately substituted aniline (a) is reacted with an ω-halo (chloride or bromide) acetyl or propionyl halide (chloride or bromide) in a solvent such as methylene chloride or acetic acid in the presence of a base such as pyridine, triethylamine or sodium acetate at a temperature of from about −20° C. to about 50° C. preferably at 0°–20° C. The resulting ω-haloacylanilide (b) is then reacted with a secondary amine either neat or in a solvent such as water or a lower alkanol at a temperature from 20° to about 120° C. preferably from about 25° to 50° C. to yield (c). In the instance wherein one of $R_4$ or $R_5$ in the final product is hydrogen, then the foregoing secondary amine will have as one of its substituents a suitable N-protecting group such as benzyl or 4-methoxybenzyl. Said protecting group can be easily removed as the very last step of the synthesis. The compound (c) is reacted with lithium aluminum hydride in a solvent such as diethyl ether or tetrahydrofuran at a temperature of from 20° to 100° C. preferably at 60°–80° C. to provide the N-aryldiamine (d). The compound (d) is then reacted with an 4-[(alkylsulfonyl)amino]benzoyl chloride to provide the final product (f). This reaction can be carried out in solvents such as tetrahydrofuran, methylene chloride or chloroform at a temperature of from −10° C. to 50° C. usually at 0° C. A base such as pyridine, collidine or triethylamine may be added to facilitate the reaction.

SCHEME B

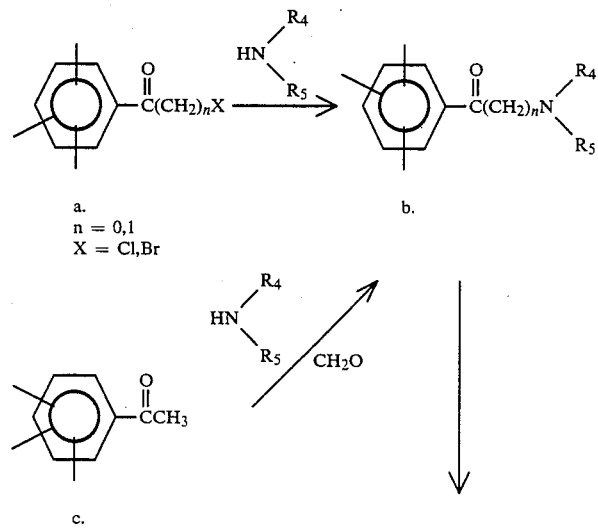

SCHEME B

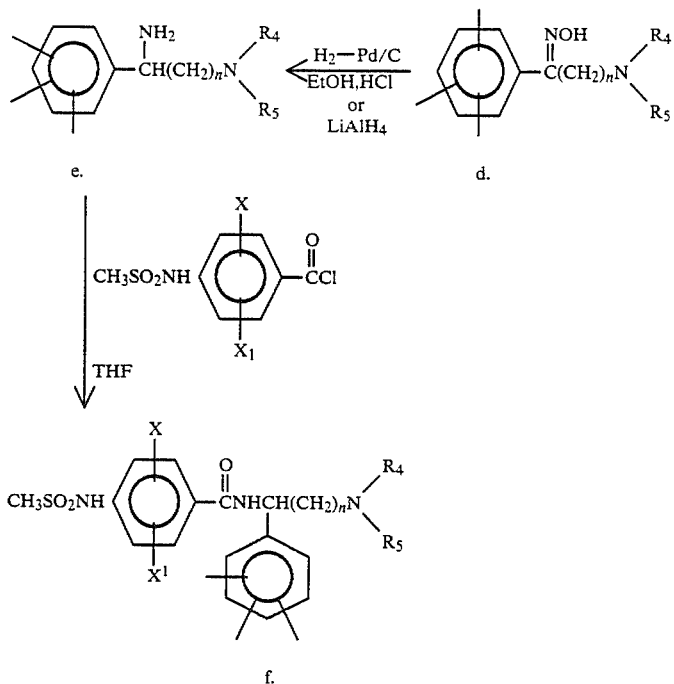

In the foregoing Scheme B is outlined a route for the preparation of the compounds wherein $R_2$ is aryl and $R_1$ and $R_3$ are hydrogen. An appropriately substituted ω-halo acetophenone or propiophenone (a) is reacted with a secondary amine in a manner similar to the described for Scheme A to produce an ω-amino aceto or propiophenone (b).

Alternatively, to obtain the β-aminopropiophenone (b) a Mannich reaction may be carried out employing the desired secondary amine, formaldehyde and acetophenone (c). A protected amine may be employed similar to that described in Scheme A. The ω-aminoketone (b) is converted to the oxime (d) by reaction with hydroxylamine hydrochloride in an aqueous base or buffered solution. The oxime (d) is reduced to the diamine (e) by hydrogenation over platinum oxide or palladium on carbon in the presence of acid at about 30–50 psi of by chemical reduction utilizing tin in hydrochloric acid, lithium aluminum hydride, etc. The diamine (e) is converted to compounds of the invention (f) by reaction with the 4-[(alkylsulfonyl)amino]benzoyl chloride as described in Scheme A.

SCHEME C

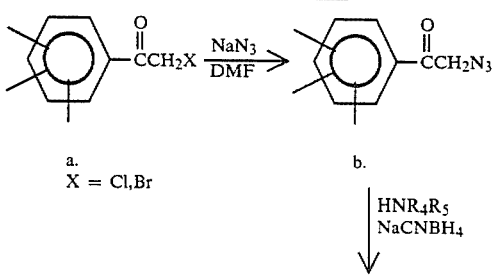

-continued SCHEME C

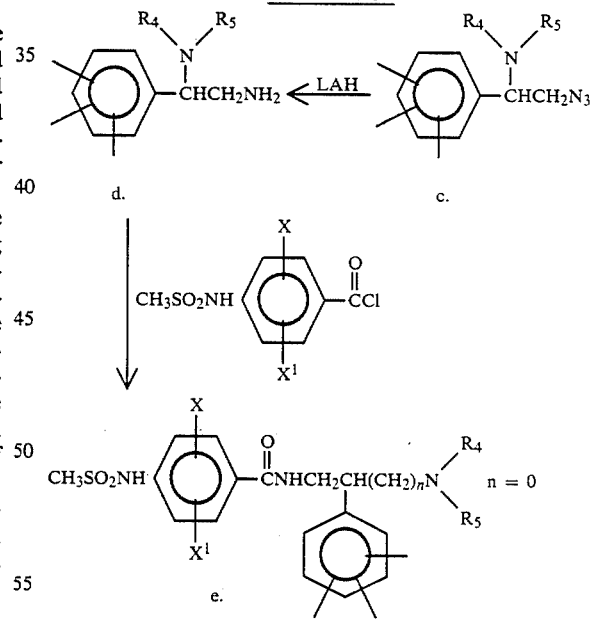

The foregoing Scheme C is illustrative of a method for the preparation of compounds of the invention wherein $R_3$ is aryl, $R_1$, $R_2$ are H and n is the integer 0.

An ω-haloacetophenone (a) is reacted with sodium azide in a solvent such as dimethylformamide, ethanol, methanol, acetone/water or acetonitrile at a temperature of about 20°–120° C. to provide the corresponding ω-azidoacetophenone (b). Reductive amination of (b) under Borch conditions using sodium cyanoborohydride and a secondary amine in dry methanol provides an aminoazide (c). Again as described in the previous schemes, protected amines may be utilized. The azido group of (c) is reduced to the primary amine by reaction with lithium aluminum hydride under conditions outlined in Scheme A. Reaction of the resultant diamine (d) with 4-[(alkylsulfonyl)amino]benzoyl chloride as in Scheme A provides compounds of the invention (e).

effect. Such combination contains those therapeutic effects attributed to Class I and Class III agents singly.

That is, they both slow conduction and prolong ventricular refractoriness in cardiac tissue.

The classification of various antiarrhythmic agents has been made easier since Vaughan Williams in 1970

SCHEME D

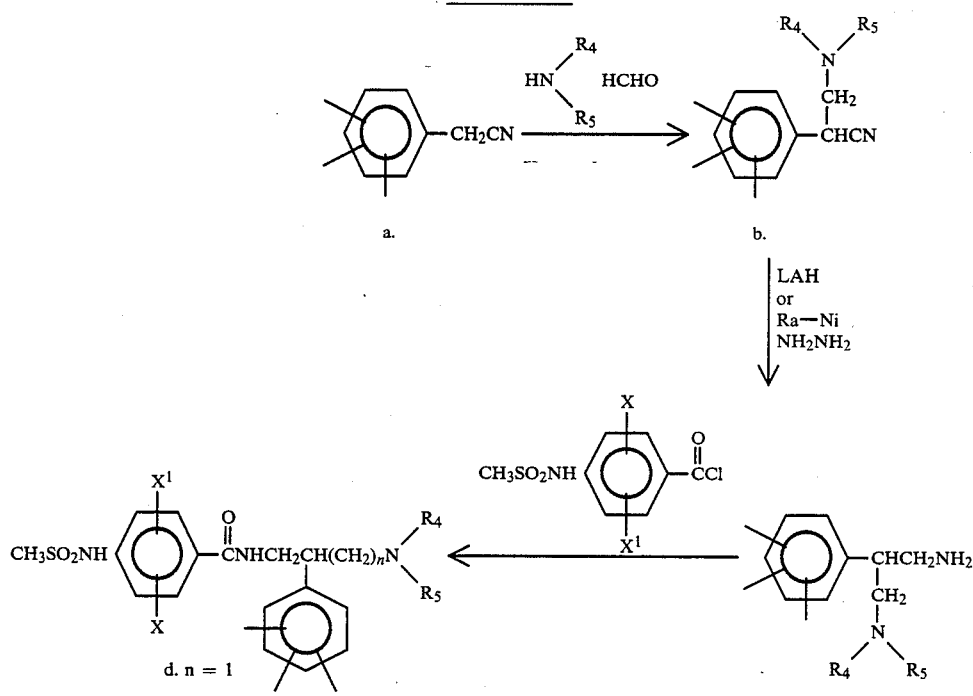

Scheme D illustrates the method for preparing compounds of the invention wherein $R_3$ is aryl, $R_1$ and $R_2$ are hydrogen and n is the integer 1. Mannich reaction of a phenylacetonitrile (a) with formaldehyde and a secondary amine affords an aminonitrile (b). Reduction of compound (b) to a diamine (c) can be carried out with either lithium aluminum hydride or by reaction with hydrazine in aqueous ethanol in the presence of Raney nickel. The reaction with hydrazine is carried out at a temperature of 20°–80° C., preferably at about 50°–60° C. The diamine (c) is acylated as described in Scheme C to afford compounds (d).

Certain of the compounds of the invention contain asymmetric carbon atoms and as such may be prepared as their optically active or racemic components. Preparation of enantiomerically pure materials may be accomplished where necessary either by resolution of the racemate using an optically active acid, such as (+) tartaric acid, (−) camphorsulfonic acid, etc. or by resolution of one of the intermediate amines or diamines in a similar manner then completion of the synthesis with enantiomerically pure intermediates.

METHOD-OF-USE AND PHARMACEUTICAL COMPOSITION ASPECT

The novel N-(aminoalkyl)-subtituted(N or C alkyl)-aryl-4(methylsulfonylamino)benzamides of this invention and their pharmaceutically acceptable salts are antiarrhythmic agents. These compounds are useful in the treatment of cardiac arrhythmias most especially these compounds have been designed to provide a combination Class I/Class III antiarrhythmic therapeutic devised his method for classifying said agents. Generally speaking, Class I agents typified for example by flecainide, lidocaine or mexiletine are local anesthetics on nerve and myocardial membranes thereby slowing conduction which decreases the propagation of ectopic (premature) beats and suppresses the tendency of damaged cells to initiate ectopic beats. The Class II agents are the so-called β-blockers best exemplified by propranolol. The Class III agents represented by bretylium, clofilium or sematilide have little or no effect on conduction, in fact, they are quite independent of conduction. They prolong the action potential duration of the heart thus increasing the time interval in which the heart is unexcitable (refractory period) without slowing conduction or changing the excitability of the cardiac cells.

With such drugs available, the medical community dealing with cardiovascular abnormalities has a large armamentarium from which to choose the therapy needed for a given situation.

In general, after a myocardial infarct the patient is treated with a Class I agent to slow conduction because cardiac cells in the border zone of the infarcted region of the heart are electrically unstable, giving rise to ecotopic beats resulting in the appearance of numerous PVC's (premature ventricular contractions).

As the patients' infarct heals the tissue substrate for arrhythmia may change and potentially a re-entrant pathway may be established leading to ventricular tachycardias—which condition may be treated with a Class III agent. Such an agent prolongs ventricular refractoriness in cardiac tissue.

However, there are numerous instances when the physician must deal with patients whose treatmenttheraphy calls for the use of both a Class I and Class III agent.

Recent clinical experience has demonstrated that combinations of certain antiarrhythmic agents may yield greater efficacy than if each is used alone. For example, the enhanced response of patients to combinations of drugs during programmed electrical stimulation studies in the clinical setting. However, use of two agents potentially increases the problems in multiple drug therapy, e.g., side effects, metabolic problems, drug interactions etc. and the problems in patient compliance—different drugs, different therapeutic regimens.

Contrariwise the compounds of this invention provide the physician with a single chemical entity evoking both Class I and Class III antiarrhythmic effects.

Compounds of this invention exemplified by N-[2-(diethylamino)ethyl]-N-[2,6-bis(1-methylethyl)phenyl]-4-[(methylsulfonyl)amino]benzamide hydrochloride and N-[2-(diethylamino)-1-(1-naphthalenyl)ethyl]-4-[(methylsulfonyl)amino]benzamide have been analyzed in several biological procedures. For instance, utilizing standard electrophysiological techniques, the resting potential, amplitude, duration, rate of rise of phase 0 (depolarization) of the action potential are measured in normal canine Purkinje fibers. The aforenamed compounds in this screen increased the action potential duration and decreased the rate of rise of phase 0 (i.e. slowed conduction). The former response is indicative of the Class III agent and the latter of the Class I agent.

To better understand the activity of the compounds of this invention 5 compounds were tested and compared, the results of which are illustrated in the following Table I:

pound B all exhibit Class I antiarrhythmic effects whilst the Class III agents sematilide and clofilium are inactive—even up to 10 mg/kg.

In the Harris dog model, a decrease in ectopic activity is considered efficacious and demonstrates Class I activity, flecainide, compound A and compound B all decrease the ectopic activity whereas the Class III agents sematilide and clofilium were inactive in this model.

The PES-induced arrhythmia model illustrates that flecainide a Class I agent is inactive whilst sematilide, clofilium, compound A & compound B all manifest Class III antiarrhythmic effects.

Thus, the foregoing data illustrate that the compounds of this invention as exemplified by compounds A and B clearly show the combination of Class I and Class III antiarrhythmic effects in contradistinction to the selective Class I flecainide which shows no Class III effect and clofilium and sematilide selective Class III agents which show no Class I effects.

Thus, there is provided by this invention a method for treating arrhythmias which comprises administering to a subject suffering from arrhythmias and in need of treatment or to a subject suspected of developing said arrhythmias an effective amount for treating such arrhythmias of a compound of this invention. The compounds are preferably utilized for the control of those arrhythmias most generally treated with Class I and Class III type antiarrhythmic agents, thus vitiating the need for 2 compound therapy.

In general, the compounds of this invention may be administered orally or parenterally. The dosage administered will be dependent on the subject being treated, the route of administration and the type and severity of the arrhythmias being prevented or reduced.

The compound to be administered can be formulated

TABLE I

|  | Class I | Class III | | Class I/III | Class I/III |
|---|---|---|---|---|---|
|  | Flecainide | Sematilide | Clofilium | Compound A | Compound B |
| 1. Ouabain Guinea Pig Model |  |  |  |  |  |
| Percent Increase in Time to Arrhythmia | +51% @ 3 mpk | <+5% @ 10 mpk | <+5% @ 10 mpk | 22% @ 3 mpk | 70% @ 3 mpk |
| 2. Harris Dog Model |  |  |  |  |  |
| Percent Ectopic | Cont - 91+/−1% 1 mpk - 72+/−3% | Cont - 86+/−1% 1 mpk - 91+/−1% | Cont - 93+/−1% 0.3 mpk - 94+/−1% | Cont - 92+/−1% 1 mpk - 99+/−1% | Cont - 98+/−1% 1 mpk - 90+/−2% |
| Beats | 2.5 mpk - 52+/−3% 5 mpk - 48+/−6% | 3 mpk - 89+/−1% 10 mpk - 87+/−1% | 1 mpk - 94+/−1% 3 mpk - 93+/−1% | 3 mpk - 88+/−2% 10 mpk - 69+/−7% | 2 mpk - 64+/−4% 4 mpk - 13+/−4% |
| 3. PES-induced Arrhythmias |  |  |  |  |  |
| Efficacy | 2/8 Not Active | 5/6 @ −1 mpk, iv | 5/6 @ 1 mpk, iv | 4/5 @ 1 mpk, iv | 4/7 @ 1 mpk, iv |

The 5 compounds which were compared are flecainide—a Class I agent, clofilium—a Class III agent, sematilide—a Class III agent, compound A - N-[2-(Diethylamino)ethyl]-N-[2,6-bis(1-methylethyl)phenyl]—4-[(methylsulfonyl)amino]benzamide hydrochloride—a Class I/III agent and compound B - N-[2-(Diethylamino)-1-(1-naphthalenyl)ethyl]-4-[(methylsulfonyl)amino]benzamide—a Class I/III agent.

The above 5 compounds were tested (a) in the ouabain guinea pig model—to assess their Class I effects (b) in the Harris Dog model to test their Class I effects and (c) in the PES-induced arrhythmia model to test their Class III effects.

As can be ascertained from Table I in the ouabain guinea pig model, flecainide, compound A and comby admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention for example, N-[2-(diethylamino)ethyl]-N-[2,6-bis(1-methylethyl)phenyl]-4-[(methylsulfonyl)amino]-benzamide hydrochloride or N-[2-(diethylamino)-1-(1-naphthalenyl)ethyl]-4-[(methylsulfonyl)aminobenzamide in the amount of about 1 to about 500 mg. Such formulation can be administered orally at the rate of about 1 to 4 capsules per day or more often as needed, depending upon the particular condition and subject being treated.

For parenteral administration a compound of this invention can be formulated as an intramuscular or intravenous medicament but is not limited thereto. In the case of treatment of a patient suffering from severe cardiac arrhythmias, it may be desirable to administer a compound of the invention by intravenous slow bolus in order to effect a rapid conversion to a normal sinus rhythm. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. A typical formulation suited to intravenous or intramuscular administration may contain one of the compounds of this invention such as N-[2-(diethylamino)ethyl]-N-[2,6-bis(1-methylethyl)phenyl]-4-[(methylsulfonyl)amino]benzamide hydrochloride or N-[2-(diethylamino)-1-(1-naphthalenyl)ethyl]-4-[(methylsulfonyl)amino]benzamide in the amount of about 50 to 150 mg and a solubilizing agent and sufficient sterile water to bring the volume to about 5 ml–100 ml. Such formulation can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical preparations of the compounds of this invention may optionally, additionally contain one or more other pharmaceutically active substances. As for instance combining the compounds of this invention with β-adrenergic blocking agents for the treatment of mammalian subjects who have suffered myocardial infraction.

The invention described hereinabove is illustrated below in the Preparations and Examples, which, however, are not to be construed as limiting the scope of this invention.

PREPARATIONS

Preparation 1

2-(Diethylamino)-N-(2,6-bis(1-methylethyl)phenyl)acetamide

To 325 mL of acetic acid under a nitrogen atmosphere add 60.0 g (0.338 mol) of 2,6-bis(1-methylethyl)benzenamine and 42.8 g (0.379 mol) of chloroacetyl chloride. Allow the reaction mixture to stir at ambient temperature for 1 hour. Add a solution of 55.4 g (0.676 mL) of sodium acetate in 325 mL of water and stir for 45 minutes. Monitor the progress of the reaction by thin-layer chromatography on silica gel (EtOAc:Hexane, 3:10). Add an additional 390 mL of water and stir the mixture for 1 hour and 15 minutes. Suction filter the resulting solid.

To 200 mL of ethanol is added 40.4 g (0.159 mol) of the solid and 35.0 g (0.478 mol) of diethylamine, reflux for 14 hours. Monitor the progress of the reaction by thin-layer chromatography on silica gel (EtOAc:Hexane, 3:10). Upon completion of the reaction remove the solvent. Add 300 mL of water and 250 mL 3N HCl and extract three times with ether. Adjust the pH of the aqueous layer to 11 with 50% sodium hydroxide and extract three times with methylene chloride. Dry the organic layer over sodium sulfate. Remove the solvent in vacuo. Recrystallize the solid from hexane to obtain the title compound.

NMR (DMSO-$d_6$): $\delta$ = 1.09(dd,18), 2.61(quar,4), 3.01(m,2), 3.14(s,2), 7.17(d,2), 7.29(m,1) and 9.13(s,1) ppm.

Preparation 2

N,N-Diethyl-N'-(2,6-bis(1-methylethyl)phenyl)-1,2-ethanediamine

To 200 mL of tetrahydrofuran under a nitrogen atmosphere add 8.8 g (0.23 mol) of lithium aluminum hydride. Add dropwise a solution of 33.8 g (0.12 mol) of 2-(diethylamino)-N-(2,6-bis(1-methylethyl)phenyl)acetamide in 150 mL of tetrahydrofuran. When the addition is complete allow the reaction to stir at reflux. Monitor the progress of the reaction by thin-layer chromatography on silica gel ($CH_2Cl_2$:MeOH, 9:1). Upon completion of the reaction add 1 mL of water, 1 mL of 15% NaOH and 3 mL of water per gram of lithium aluminum hydride. The solid material is removed by suction filtration through celite and the solvent is removed in vacuo. Recrystallize the solid from hexane to give the title compound.

NMR (DMSO-$d_6$): $\delta$ = 1.10(t,6), 1.15(m,12), 2.49(m,4), 2.58(m,2), 2.81(m,2), 3.31(m,2 and 7.0(m,3) ppm.

Preparation 3

2-Azido-1-(naphthalen-1-yl)ethanone

Combine 24.9 g (0.1 mol) of 2-bromo-1-(naphthalen-1-yl)ethanone and 24 g (0.37 mol) of sodium azide in 200 mL of 60% aqueous acetone. Heat the mixture at reflux for about 18 to 36 hr and follow the progress of the reaction by thin-layer chromatography on silica gel. At the completion of the reaction, distill off the acetone and add 25 mL of water. Extract the aqueous mixture with three 100 mL portions of diethyl ether. Dry the organic extracts over anhydrous sodium sulfate. Filter the drying agent and remove the solvent in vacuo to obtain the title compound.

Preparation 4

α-Azidomethyl-N,N-diethyl-1-naphthalenemethanamine

To a solution of 2.11 g (0.01 mol) of 2-azido-1-(naphthalen-1-yl)ethanone, and 3.66 g (0.05 mol) of diethylamine in 50 mL of dry methanol add 10 g of 3A molecular sieves. Adjust the pH of the mixture to pH=6 with 5N HCl in methanol and add 1 g (0.016 mol) of sodium cyanoborohydride. Follow the progress of the reaction by thin-layer chromatography on silica gel. Maintain the pH of the reaction mixture at pH=ca.6 by the addition of 5N HCl in methanol as necessary. At the completion of the reaction add concentrated hydrochloric acid until pH <2. Evaporate the solvent in vacuo. To the residue add 50 mL of water and extract with three 25 mL portions of diethyl ether. Adjust the pH of the aqueous phase to pH=11 with 4N sodium hydroxide solution and extract with three 100 mL portions of methylene chloride. Wash the combined extracts with 50 mL of water and 50 mL of saturated sodium chloride solution then dry over anhydrous sodium sulfate. Filter the drying agent and evaporate the solvent in vacuo to obtain the title compound.

Preparation 5

$N^1,N^1$-Diethyl-1-(naphthalen-1-yl)-1,2-ethanediamine

To a suspension of 0.76 g (0.02 mol) of lithium aluminum hydride in 100 mL of dry diethyl ether under a nitrogen atmosphere and cooled to $-10°$ to 0° C. add carefully in portions 10.67 g (0.08 mol) of aluminum chloride. When the initial reaction has ceased add dropwise a solution of 2.68 g (0.01 mol) of α-azidomethyl-N,N-diethyl-1-naphthalenemethanamine in 50 mL of diethylether. When the addition is complete allow the reaction mixture to warm to room temperature. Follow the progress of the reaction by thin-layer chromatography on silica gel. At the completion of the reaction carefully quench the excess reducing agent by the addition of sodium sulfate decahydrate. Filter the solids and wash the solids with 500 mL of hot methylene chloride. Dry the filtrate over anhydrous sodium sulfate. Filter the drying agent and remove the solvent in vacuo to obtain the title compound.

Preparation 6

2-(Diethylamino)-1-(naphthalen-1-yl)ethanone

To a solution of 38.1 g (0.52 mol) of diethylamine in 80 mL of toluene and cooled in an ice bath to 0° C. add dropwise a solution of 65.0 g (0.26 mol) of 2-bromoacetonaphthone in 300 mL of toluene. Stir the reaction mixture overnight. Monitor the progress of the reaction by thin-layer chromatography on silica gel (ethyl acetate:hexane, 1:1). Extract the reaction mixture with 3×150 mL of 3N HCl. Adjust the pH of the combined aqueous layers to pH=10 with 50% sodium hydroxide then extract with 3×150 mL of methylene chloride. Combine the extracts and dry over sodium sulfate. Remove the solvent in vacuo, and chromatograph the resultant oil on 2200 g of silica gel, eluting initially with methylene chloride and later with ethyl acetate. Combine the fractions containing product and remove the solvent in vacuo to obtain the title compound.

NMR (CDCl$_3$): δ=1.14(t,6), 2.79(quar,4), 3.99(s,2), 7.56(m,3), 7.92(m,2), 8.02(d,1) and 8.54(d,1) ppm.

Preparation 7

2-(Diethylamino)-1-(naphthalen-1-yl)ethanone oxime

To a cooled solution of 97.6 g (1.48 mol) of potassium hydroxide in 320 mL of methanol add a solution of 20.8 g (0.3 mol) of hydroxylamine hydrochloride in 48 mL of water at 20° C. To this basic solution add a solution of 16 g (0.064 mol) of 2-(diethylamino)-1-(naphthalen-1-yl)ethanone in 20.8 mL of methanol at 20° C. Stir the reaction mixture overnight. The reaction mixture is concentrated in vacuo. Add methylene chloride and extract with 3×200 mL of water. Dry the organic layer over sodium sulfate. Remove the solvent in vacuo to obtain the title compound.

NMR (CDCl$_3$): δ=0.98 and 1.18(t,total 6), 1.65(br,1), 2.65 and 2.78(quar,total 4), 3.68(br,2) and 7.4–8.2 (m,7) ppm.

Preparation 8

$N^2,N^2$-Diethyl-1-(naphthalen-1-yl)-1,2-ethanediamine

To a mixture of 12.8 g (0.05 mol) of 2-(diethylamino)-1-(naphthalen-1-yl)ethanone oxime in 30 mL of ethanol and 70 mL of concentrated hydrochloric acid carefully add 30 g (0.25 mol) of tin metal. When the evolution of hydrogen ceases, warm the mixture until a clear solution results. Dilute the reaction mixture with 300 mL of water and bubble hydrogen sulfide gas through the solution to precipitate the tin salts as tin sulfide. Filter the sulfide then reduce the volume of the filtrate to ca. 100 mL. Extract the aqueous mixture with three 50 mL portions of diethyl ether. Make the solution basic (pH=11) with concentrated ammonium hydroxide. Extract the basic mixture with three 100 mL portions of methylene chloride. Wash the combined extracts with 50 mL of water and 50 mL of saturated sodium chloride solution then dry over anhydrous sodium sulfate. Filter the drying agent and evaporate the solvent in vacuo to obtain the title compound.

Preparation 9

4-[(Ethylsulfonyl)amino]benzoic acid

To a solution of 16.5 g (0.1 mol) of ethyl 4-aminobenzoate and 16 g (0.2 mol) of pyridine in 200 mL of methylene chloride cooled to 0° C. add dropwise 13 g (0.1 mol) of ethanesulfonyl chloride. After the addition is complete stir the mixture at 20° C. for 4 hr. After this time extract the mixture with three 100 mL portions of 1N sodium hydroxide. Heat the basic extracts at reflux for 2 hr, cool to 0°–10° C. and carefully add 60 mL of concentrated hydrochloric acid. Collect the resulting precipitate to obtain the title compound.

Preparation 10

4-[(Ethylsulfonyl)amino]benzoyl chloride

To 100 mL of thionyl chloride at 0° C. is added 25.1 g (0.1 mol) of 4-[(ethylsulfonyl)amino]benzoic acid sodium salt (prepared from the acid and sodium hydroxide in water and evaporation of solvent) under a nitrogen atmosphere. Reflux the reaction mixture for 24–40 hr. then remove the excess thionyl chloride in vacuo. Dissolve the crude material in tetrahydrofuran, filter through celite and evaporate the solvent to obtain the title compound.

Preparation 11

α-(3,4-Dichlorophenyl)-1-pyrrolidinepropanenitrile

To 100 mL of ethanol is added (18.6 g (0.1 mol) 3,4-dichlorobenzeneacetonitrile, 12.6 g (0.12 mol) of pyrrolidine hydrochloride, 6.0 g (0.2 mol) of paraformaldehyde and 1 mL of concentrated hydrochloric acid. Stir the mixture at reflux. Monitor the progress of the reaction by thin-layer chromatography. Upon completion add 300 mL of 1N HCl and extract with 200 mL of Et$_2$O. Add 4N NaOH to the aqueous solution until basic and extract the aqueous solution with two 100 mL portions of CH$_2$Cl$_2$. Dry the organic phase over anhydrous Na$_2$SO$_4$. Filter the drying agent and evaporate the solvent in vacuo to obtain the title compound.

Preparation 12

β-(3,4-Dichlorophenyl)-1-pyrrolidinepropanamine

In a manner similar to Preparation 2 react β-(3,4-dichlorophenyl)-1-pyrrolidinepropanenitrile with lithium aluminum hydride to obtain the title compound.

Preparation 13

α-[(Dipropylamino)methyl]-3,4,5-trimethoxybenzeneacetonitrile

In a manner similar to Preparation 11 react 3,4,5-trimethoxybenzeneacetonitrile with dipropylamine hydrochloride and paraformaldehyde to obtain the title compound.

Preparation 14

N,N-Dipropyl-2-(3,4,5-trimethoxyphenyl)-1,3-propanediamine

In a manner similar to Preparation 2 react α-[(dipropylamino)methyl)]-3,4,5-trimethoxybenzeneacetonitrile with lithium aluminum hydride to obtain the title compound.

Preparation 15

α-(2,6-Difluorophenyl)-4-morpholinepropanenitrile

In a manner similar to Preparation 11 react 2,6-difluorobenzeneacetonitrile with morpholine hydrochloride and paraformaldehyde to obtain the title compound.

Preparation 16

β-(2,6-Difluorophenyl)-4-morpholinepropanamine

In a manner similar to Preparation 2 react α-(2,6-difluorophenyl)-4-morpholinepropaneitrile with lithium aluminum hydride to obtain the title compound.

Preparation 17

α-(2-Naphthalenyl)-4-pentylpiperazinepropanenitrile

In a manner similar to Preparation 11 react 2-naphthaleneacetonitrile with 4-pentylpiperazine hydrochloride and paraformaldehyde to obtain the title compound.

Preparation 18

β-(2-Naphthalenyl)-4-pentyl-1-piperazinepropanamine

In a manner similar to Preparation 2 react α-(2-naphthalenyl)-4-pentylpiperazinepropanenitrile with lithium aluminum hydride to obtain the title compound.

Preparation 19

N-(3-Chloro-4-methoxyphenyl)-2-[ethyl(heptyl)amino]acetamide

In a manner similar to Preparation 1 react 3-chloro-4-methoxybenezenamine with chloroacetyl chloride followed by N-ethylheptanamine to obtain the title compound.

Preparation 20

N-(3-Chloro-4-methoxyphenyl)-N'-ethyl-N'-heptyl-1,2-ethanediamine

In a manner similar to Preparation 2 react N-(3-chloro-4-methoxyphenyl)-2-[ethyl(heptyl)amino]acetamide with lithium aluminum hydride to obtain the title compound.

Preparation 21

N-(2-Propenyl)cyclohexanemethanamine

To 100 mL of MeOH is added 2-propenylamine (5.7 g, 0.1 mol), 11.2 g (0.1 mol) of cyclohexane carboxaldehyde and 12 g (0.2 mol) of NaBH$_3$CN. The pH is adjusted to 6 with concentrated HCl. Monitor the reaction by thin layer chromatography. Upon completion add concentrated HCl until gas evolution ceases. Add 300 mL of H$_2$O and extract once with 200 mL of Et$_2$O. Add 1N NaOH to the aqueous solution until it is basic (pH=11) and extract 2 times with 200 mL of Et$_2$O. Dry the organic phase over Na$_2$SO$_4$. Filter the drying agent and evaporate the solvent in vacuo to obtain the title compound.

Preparation 22

N-(2-Chloro-4-methoxyphenyl)-2-[cyclohexylmethyl(2-propenyl)amino]acetamide

In a manner similar to Preparation 1 react 2-chloro-4-methoxybenzenamine with chloroacetyl chloride followed by N-(2-propenyl)cyclohexanemethanamine to obtain the title compound.

Preparation 23

N-(2-Chloro-4-methoxyphenyl)-N'-(cyclohexylmethyl)-N'-(2-propenyl)-1,2-ethanediamine In a manner similar to Preparation 2 react N-(2-chloro-4-methoxyphenyl)-2-[cyclohexylmethyl(2-propenyl)-amino]acetamide with lithium aluminum hydride to obtain the title compound.

Preparation 24

N-[4-(1,1-Dimethyethyl)phenyl]-4-morpholinepropanamide

In a manner similar to Preparation 1 react 4-(1,1-dimethylethyl)benzenamine with 3-chloropropanoyl chloride followed by morpholine to obtain the title compound.

Preparation 25

4-(1,1-Dimethylethyl)-N-[3-(morpholin-4-yl)propyl]-benzenamine

In a manner similar to Preparation 2 reaction N-[4-(1,1-dimethylethyl)phenyl]-4-morpholinepropanamide with lithium aluminum hydride to obtain the title compound.

Preparation 26

3,4-Dimethoxybenzeneethanamine

In a manner similar to Preparation 2 react 3,4-dimethoxybenzeneacetonitrile with lithium aluminum hydride to obtain the title compound.

Preparation 27

3,4-Dimethoxy-N-methylbenzeneethanamine

In a manner similar to Preparation 21 react 3,4-dimethoxybenzeethanamine with aqueous formaldehyde and sodium cyanoborohydride to obtain the title compound.

Preparation 28

N-[4-Butoxyphenyl]-3-[[2-(3,4-dimethoxyphenyl)ethyl](methyl)amino]propionamide

In a manner similar to Preparation 1 react 4-butoxybenezenamine with 3-chloropropanoyl chloride followed by 3,4-dimethoxy-N-methylbenzeneethanamine to obtain the title compound.

Preparation 29

N-[4-Butoxyphenyl]-N'-[2-(3,4-dimethoxyphenyl)ethyl]-N'-methyl-1,3-propanediamine In a manner similar to Preparation 2 react N-[4-butoxyphenyl]-3-[[2-(3,4-dimethoxyphenyl)ethyl](methyl)amino]propionamide with lithium aluminum hydride to obtain the title compound.

Preparation 30

2-Bromo-1-(2,4-dichlorophenyl)ethanone

To 100 mL of ethyl ether is added 1-(2,4-dichlorophenyl)ethanone (18.9 g, 0.1 mol) and bromine (16 g, 0.1 mmol). Monitor the reaction by thin-layer chromatography. Upon completion wash the organic phase with 100 mL $H_2O$ and 50 mL brine. Dry the organic phase over $Na_2SO_4$. Filter the drying agent and evaporate the solvent in vacuo to obtain the title compound.

Preparation 31

2-Azido-1-(2,4-dichlorophenyl)ethanone

In a manner similar to Preparation 3 react 2-bromo-1-(2,4-dichlorophenyl)ethanone with sodium azide to obtain the title compound.

Preparation 32

1-[2-Azido-1-(2,4-dichlorophenyl)ethyl]piperidine

In a manner similar to Preparation 21 react 2-azido-1-(2,4-dichlorophenyl)ethanone with piperidine and $NaCNBH_3$ to obtain the title compound.

Preparation 33

β-(2,4-Dichlorophenyl)-1-piperidineethanamine

In a manner similar to Preparation 5 react 1-[2-azido-1-(2,4-dichlorophenyl)ethyl]piperidine with lithium aluminum hydride and aluminum chloride to obtain the title compound.

Preparation 34

2-Bromo-1-(3,4,5-trimethoxyphenyl)ethanone

In a manner similar to Preparation 30 react 1-(3,4,5-trimethoxyphenyl)ethanone with bromine to obtain the title compound.

Preparation 35

2-Azido-1-(3,4,5-trimethoxyphenyl)ethanone

In a manner similar to Preparation 3 react 2-bromo-1-(3,4,5-trimethoxyphenyl)ethanone with $NaN_3$ to obtain the title compound.

Preparation 36

α-(Azidomethyl)-N-cyclohexyl-3,4,5-trimethoxybenzenemethanamine

In a manner similar to Preparation 21 react 2-azido-1-(3,4,5-trimethoxyphenyl)ethanone with cyclohexanamine and $NaCNBH_3$ to obtain the title compound.

Preparation 37

$N^1$-Cyclohexyl-1-(3,4,5-trimethoxyphenyl)-1,2-ethanediamine

In a manner similar to Preparation 5 react α-(azidomethyl)-N-cyclohexyl-3,4,5-trimethoxybenzenemethanamine with lithium aluminum hydride and aluminum chloride to obtain the title compound.

Preparation 38

N-(4-Fluorophenyl)-2-[(2-phenylethyl)(phenylmethyl)amino]acetamide

In a manner similar to Preparation 1 react 4-fluorobenzenamine with chloroacetyl chloride followed by N-(phenylmethyl)benzeneethanamine to obtain the title compound.

Preparation 39

N-(4-Fluorophenyl)-N'-(2-phenylethyl)-N'-phenylmethyl-1,2-ethanediamine

In a manner similar to Preparation 2 react N-(4-fluorophenyl)-2-[(2-phenylethyl)(phenylmethyl)amino]acetamide with lithium aluminum hydride to obtain the title compound.

Preparation 40

2-Diethylamino-1-(3,4,5-trimethoxyphenyl)ethanone

To 100 mL of EtOH is added 28.9 g (0.1 mol) of 2-bromo-1-(3,4,5-trimethoxyphenyl)ethanone and 9.0 g (0.2 mol) of diethylamine. Reflux the reaction mixture and monitor by thin-layer chromatography. Upon completion of the reaction remove the solvent in vacuo and add 100 mL of 5% $Na_2CO_3$ solution and extract with $Et_2O$. Dry the organic layer with $Na_2SO_4$. Filter off the drying agent and evaporate the solvent in vacuo to obtain the title compound.

Preparation 41

$N^1$,$N^1$-Diethyl-2-(3,4,5-trimethoxyphenyl)-1,2-ethanediamine

In a manner similar to Preparation 21 react 2-diethylamino-1-(3,4,5-trimethoxyphenyl)ethanone with ammonium acetate and $NaCNBH_3$ to obtain the title compound.

Preparation 42

1-(2,4-Dichlorophenyl)-2-(dimethylamino)ethanone

In a manner similar to Preparation 40 react 2-bromo-1-(2,4-dichlorophenyl)ethanone with dimethylamine to obtain the title compound.

Preparation 43

1-(2,4-Dichlorophenyl)-$N^2$,$N^2$-dimethyl-1,2-ethanediamine

In a manner similar to Preparation 21 react 1-(2,4-dichlorophenyl)-2-(dimethylamino)ethanone with $NH_4OAc$ and $NaCNBH_3$ to obtain the title compound.

Preparation 44

4-[(1-Propylsulfonyl)amino]benzoic acid

In a manner similar to Preparation 9 react ethyl 4-aminobenzoate with 1-propanesulfonyl chloride and pyridine to obtain the title compound.

Preparation 45

4-[(1-Propylsulfonyl)amino]benzoyl chloride

In a manner similar to Preparation 10 react 4-[(1-propylsulfonyl)amino]benzoic acid with $SOCl_2$ to obtain the title compound.

Preparation 46

4-[(1-Butylsulfonyl)amino]benzoic acid

In a manner similar to Preparation 9 react ethyl 4-aminobenzoate with 1-butanesulfonyl chloride and pyridine to obtain the title compound.

Preparation 47

4-[(1-Butylsulfonyl)amino]benzoyl chloride

In a manner similar to Preparation 10 react 4-[(1-butylsulfonyl)amino]benzoic acid with $SOCl_2$ to obtain the title compound.

EXAMPLES

Example I

N-[2-(Diethylamino)ethyl]-N-(2,6-dimethylphenyl)-4-[(methylsulfonyl)amino]benzamide hydrochloride To 15 mL of tetrahydrofuran under nitrogen atmosphere add 0.74 g (4.7 mmol) of 4-[(methylsulfonyl)amino]benzoyl chloride then add 0.89 g (0.40 mmol) of N,N-diethyl-N'-(2,6-dimethylphenyl)-1,2-ethanediamine. When the addition is complete allow the reaction to stir at reflux. Monitor the progress of the reaction by thin-layer chromatography (concentrated aqueous ammonium hydroxide: acetonitrile, 1:9). Upon completion of the reaction, cool the mixture to room temperature. Filter the resulting solid and wash the solid with tetrahydrofuran. Recrystallize from acetonitrile to provide the title compound.

NMR (DMSO-$d_6$): δ=1.24(t,6), 2.18(s, 6), 2.50(t,2), 2.99(s,3), 3.19(m,4), 4.0(m,2), 6.97(d,2), 7.10–7.17(m,5), 10.10(s,1), and 10.6(brs,1)ppm.

Example II

N-[2-(Diethylamino)ethyl]-4-[(methylsulfonyl)amino]-N-(phenyl)benzamide hydrochloride In a manner similar to Example I react N,N-diethyl-N'-phenyl-1,2-ethanediamine with 4-[(methylsulfonyl)amino]benzoyl chloride to obtain the title compound.

NMR (DMSO-$d_6$): δ=1.21(t,6), 2.98(s,3), 3.20(m,6) 4.19(t,2), 7.00(d,2), 7.25(m,5), 7.34(m,2)ppm.

Example III

N-[2-(Diethylamino)ethyl]-4-[(methylsulfonyl)amino]-N-(1-napthaleny)benzamide hydrochloride In a manner similar to Example I react N,N-diethyl-N'-(1-naphthalenyl)-1,2-ethanediamine with 4-[(methylsulfonyl)amino]benzoyl chloride to obtain the title compound.

NMR (DMSO-$d_6$): δ=1.20(m,6), 2.91(s,3), 3.10–3.60 (m,6), 3.73(m,1), 4.64(m,1), 6.81(d,2), 7.17(d,2), 7.51(m,2), 7.65(t,1), 7.70(t,1), 7.92(d,1), 8.00(t,2), 9.93(brs,1), 10.34 (brs,1)ppm.

Example IV

N-[2-(Diethylamino)ethyl]-N-[2,6-bis(1-methylethyl)phenyl]-4-[(methylsulfonyl)amino]benzamide hydrochloride In a manner similar to Example I react N-[2,6-bis(1-methylethyl)phenyl]-N',N'-diethyl-1,2-ethanediamine with 4-[(methylsulfonyl)amino]benzoyl chloride to obtain the title compound.

NMR (DMSO-$d_6$): δ=8.90(d,6), 1.26(d,6), 1.31(t,6), 2.96(m,2), 2.99(s,3), 3.24(m,4), 3.38(m,2), 4.05 (m,2), 7.02(d,2), 7.17(d,2), 7.28(d,2), 7.39(m,1), 10.17(s,1), 10.88(br,1)ppm.

Example V

N-[(2-Diethylamino-1-phenyl)ethyl]-4-[(methylsulfonyl)amino]benzamide hydrochloride In a manner similar to Example I react $N^2,N^2$-diethyl-1-phenyl-1,2-ethanediamine with 4-[(methylsulfonyl)amino]benzoyl chloride to obtain the title compound.

NMR (DMSO-$d_6$): δ=1.27(t,6), 3.07(s,3), 3.24(m,4), 3.34(m,1), 3.8(m,1), 5.55(m,1), 7.34(m,5), 7.55 (d,2), 8.04(d,2), 9.38(d,1), 9.80(m,1), 10.22(s,1)ppm.

Example VI

In a manner similar to Example I react the appropriate 4-[(methylsulfonyl)amino]benzoyl chloride with the following reactants respectively:
(a) $N^2,N^2$-diethyl-1-(naphthalen-1-yl)-1,2-ethanediamine.
(b) $N^1,N^1$-diethyl-1-(napthalen-1-yl)-1,2-ethanediamine.
(c) β-(3,4-dichlorophenyl)-1-pyrrolidinepropanamine.
(d) N,N-dipropyl-2-(3,4,5-trimethoxyphenyl)-1,3-propanediamine.
(e) N-[4-(1,1-dimethylethyl)phenyl]-4-morpholinepropanamine.
(f) N-[4-butoxyphenyl]-N'-[2-(3,4-dimethoxyphenyl)ethyl]-N'-methyl-1,3-propanediamine.
(g) β-(2,4-dichlorophenyl)-1-piperidineethanamine.
(h) N,N-diethyl-2-(3,4,5-trimethoxyphenyl)-1,2-ethanediamine.
(i) 1-(2,4-dichlorophenyl)-$N^2,N^2$-dimethyl-1,2-ethanediamine.

to provide the following compounds respectively:
(j) N-[2-(diethylamino)-1-(naphthalen-1-yl)ethyl]-4-[(methylsulfonyl)amino]benzamide hydrochloride.
(k) N-[2-(diethylamino)-2-(naphthalen-1-yl)ethyl]-4-[(methylsulfonyl)amino]benzamide hydrochloride.
(l) N-[2-(3,4-dichlorophenyl)-3-(pyrrolidin-1-yl)propyl]-4-[(methylsulfonyl)amino]benzamide hydrochloride.
(m) N-[3-(dipropylamino)-2-(3,4,5-trimethoxyphenyl)propyl]-3-methyl-4-[(methylsulfonyl)amino]benzamide hydrochloride.
(n) N-[4-(1,1-dimethylethyl)phenyl]-4-[(methylsulfonyl)amino]-N-[3-(morpholin-4-yl)propyl]benzamide hydrochloride.
(o) N-[4-butoxyphenyl]-N-[3-[[2-(3,4-dimethoxyphenyl)ethyl](methyl)amino]propyl]-4-[(methylsulfonyl)amino]benzamide hydrochloride.
(p) N-[2-(2,4-dichlorophenyl)-2-(piperidin-1-yl)ethyl]-4-[(methylsulfonyl)amino]benzamide hydrochloride.
(q) N-[2-(diethylamino)-1-(3,4,5-trimethoxyphenyl)ethyl]-4-[(methylsulfonyl)amino]benzamide hydrochloride.
(r) N-[1-(2,4-dichlorophenyl)-2-(dimethylamino)ethyl]-4-[(methylsulfonyl)amino]benzamide hydrochloride.

Example VII

In a manner similar to Example I react the following:
(a) β-(2,6-difluorophenyl)-4-morpholinepropanamine and 4-[(ethylsulfonyl)amino]benzoyl chloride.
(b) β-(2-naphthalenyl)-4-pentyl-1-piperazinepropanamine and 4-[(propylsulfonyl)amino]benzoyl chloride.
(c) N-(3-chloro-4-methoxyphenyl)-N'-ethyl-N'-heptyl-1,2-ethanediamine and 4-[(butylsulfonyl)amino]benzoyl chloride.

(d) N-(2-chloro-4-methoxyphenyl)-N'-(cyclohexylmethyl)-N'-(2-propenyl)-1,2-ethanediamine and 4-[(propylsulfonyl)amino]benzoyl chloride.
(e) N¹-cyclohexyl-1-(3,4,5-trimethoxyphenyl)-1,2-ethanediamine and 4-[(ethylsulfonyl)amino]benzoyl chloride.

to provide the following products respectively:

(f) N-[2-(2,6-difluorophenyl)-3-(morpholin-4-yl)propyl]-4-[(ethylsulfonyl)amino]benzamide hydrochloride.
(g) N-[2-(2-naphthalenyl-3-(4-pentylpiperazin-1-yl)propyl]-4-[(propylsulfonyl)amino]benzamide hydrochloride.
(h) 4-[(butylsulfonyl)amino]-N-(3-chloro-4-methoxyphenyl)-N-[2-[ethyl(heptyl)amino]ethyl]benzamide hydrochloride.
(i) N-(2-chloro-4-methoxyphenyl)-N-[2-[cyclohexylmethyl(2-propenyl)amino]ethyl]-[(propylsulfonyl)amino]benzamide hydrochloride.
(j) N-[2-(cyclohexylamino)-2-(3,4,5-trimethoxyphenyl)ethyl]-4-[(ethylsulfonyl)amino]benzamide hydrochloride.

Example VIII

N-(4-Fluorophenyl)-4-[(methylsulfonyl)amino]-N-[2-[(2-phenylethyl)(phenylmethyl)amino]ethyl]benzamide hydrochloride In a manner similar to Example 1 react N-(4-fluorophenyl)-N'-(2-phenylethyl)-N'-phenylmethyl-1,2-ethanediamine with 4-[(methylsulfonyl)amino]benzoyl chloride to obtain the title compound.

Example IX

N-(4-fluorophenyl)-4-[(methylsulfonyl)amino]-N-[2-[(2-phenylethyl)amino]ethyl]benzamide hydrochloride.

Hydrogenate N-(4-fluorophenyl)-4-[(methylsulfonyl)amino]-N-[2-[(2-phenylethyl)(phenylmethyl)amino]ethyl]benzamide hydrochloride over palladium on carbon in ethanol at 30–40 psi. Follow the progress of the reaction by thinlayer chromatography on silica gel. At the completion of the reaction remove the catalyst by filtration and evaporate the solvent in vacuo to obtain the title compound.

We claim:

1. A member selected from the group consisting of a compound of the formula:

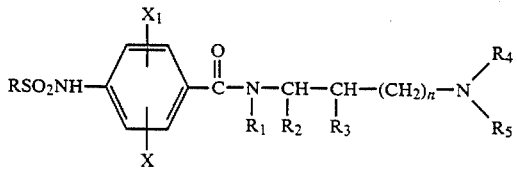

wherein
R is a $C_1$–$C_4$ straight chain alkyl;
two of $R_1$, $R_2$ and $R_3$ are hydrogen and the other is phenyl, substituted phenyl, naphthalenyl and substituted naphthalenyl;
$R_4$ and $R_5$ are hydrogen, $C_1$–$C_8$ straight or branched chain alkyl, allyl, cycloalkyl, cycloalkyl(lower)alkyl, phenyl(lower)alkyl, substituted phenyl(lower)alkyl or together with the amino nitrogen atom form a saturated heterocyclic ring of from 4 to 8 ring members or a corresponding ring which contains a —O— or

linkage;
$R_6$ is hydrogen, $C_1$–$C_8$ straight or branched chain alkyl, phenyl or substituted phenyl,
$X, X_1$ are the same or independently hydrogen and $C_1$–$C_4$ straight or branched chain alkyl; and
n is the integer 0 or 1; the word substituted in each occurrence means bearing 1 to 3 substituents selected from the group consisting of $C_1$–$C_4$-alkyl, $C_1$–$C_4$-alkoxy, trifluoromethyl, fluorine, chlorine and bromine, and the pharmaceutically acceptable salts thereof; with the proviso that only one of $R_4$ and $R_5$ can be hydrogen.

2. A compound of claim 1 wherein $R_2$ and $R_3$ are hydrogen.

3. A compound of claim 1 wherein $R_1$ and $R_3$ are hydrogen.

4. A compound of claim 1 wherein $R_1$ and $R_2$ are hydrogen.

5. A compound of claim 2 which is N-[2-(diethylamino)ethyl]-N-(2,6-dimethylphenyl)-4-[(methylsulfonyl)amino]benzamide.

6. A compound of claim 2 which is N-[2-(diethylamino)ethyl]-4-[(methylsulfonyl)amino]-N-(phenyl)benzamide.

7. A compound of claim 2 which is N-[2-(diethylamino)ethyl]-4-[(methylsulfonyl)amino]-N-(1-Napthalenyl)benzamide.

8. A compound of claim 2 which is N-[2-(diethylamino)ethyl]-N-[2,6-bis(1-methylethyl)phenyl]-4-[(methylsulfonyl)amino]benzamide.

9. A compound of claim 2 which is 4-[(butylsulfonyl)amino]-N-[3-chloro-4-methoxyphenyl]-N-[2-[ethyl(heptyl)amino]ethyl]benzamide.

10. A compound of claim 2 which is N-[2-chloro-4-methoxyphenyl]-N-[2-[(2-propenyl)(cyclohexylmethyl)amino]ethyl]-4-[(propylsulfonyl)amino]benzamide.

11. A compound of claim 2 which is N-[4-(1,1-dimethylethyl)phenyl]-4-[(methylsulfonyl)amino]-N-[3-(4-morpholinyl)propyl]benzamide.

12. A compound of claim 2 which is N-[4-butoxyphenyl]-N-[3-[(2-(3,4-dimethoxyphenyl)ethyl)(methyl)amino]propyl]-4-[(methylsulfonyl)amino]benzamide.

13. A compound of claim 2 which is N-[4-fluorophenyl]-4-[(methylsulfonyl)amino]-N-[2-[(2-phenylethyl)amino]ethyl]benzamide.

14. A compound of claim 3 which is N-[2-(diethylamino)-1-(phenyl)ethyl]-4-[(methylsulfonyl)amino]benzamide.

15. A compound of claim 3 which is N-[2-(diethylamino)-1-(naphthalen-1-yl)ethyl]-4-[(methylsulfonyl)amino]benzamide.

16. A compound of claim 4 which is N-[2-(diethylamino)-2-(1-napthalenyl)ethyl]-4-[(methylsulfonyl)amino]benzamide.

17. A compound of claim 4 which is N-[2-(3,4-dichlorophenyl)-3-(1-pyrrolidinyl)propyl]-4-[(methylsulfonyl)amino]benzamide.

18. A compound of claim 4 which is N-[3-(dipropylamino)-2-(3,4,5-trimethoxyphenyl)propyl]-3-methyl-4-[(methylsulfonyl)amino]benzamide.

19. A compound of claim 4 which is N-[2-(2,6-difluorophenyl)-3-(4-morpholinyl)propyl]-4-[(ethylsulfonyl)amino]benzamide.

20. A compound of claim 4 which is N-[2-(2-naphthalenyl)-3-(4-pentylpiperazin-1-yl)propyl]-4-[(propylsulfonyl)amino]benzamide.

21. A compound of claim 4 which is N-[2-(2,4-dichlorophenyl)-2-piperidin-1-yl ethyl]-4-[(methylsulfonyl)amino]benzamide.

22. A compound of claim 4 which is N-[2-[(cyclohexylmethyl)amino]-2-(3,4,5-trimethoxyphenyl)ethyl]-4-[(ethylsulfonyl)amino]benzamide.

23. The method for treating arrhythmias in a mammalian subject in need thereof comprising administering to said subject an anti-arrhythmically effective dose of a compound according to claim 1.

24. A pharmaceutical composition for treating arrhythmias comprising an antiarrhythmic effective amount of a compound of claim 1 together with a non-toxic pharmaceutically acceptable carrier.

* * * * *

UNITED STATES PATENT AND TRADEMARK OFFICE
CERTIFICATE OF CORRECTION

PATENT NO. : 4,920,116　　　　　　　　　　　　　　Page 1 of 2

DATED : April 24, 1990

INVENTOR(S) : Thomas K. Morgan, Jr., et al.

It is certified that error appears in the above-identified patent and that said Letters Patent is hereby corrected as shown below:

Column 7, line 50
"about 30-50 psi of" should read
---- about 30-50 psi or ----.

Column 11, line 2
"whose treatmenttherapy" should read
---- whose treatment/therapy ----.

Column 11, line 52

"5/6
@ -1 mpk, iv" should read
---- 5/6
　　@ ~1 mpk, iv ----.

Column 17, line 29
"morpholinepropaneitrile" should read
---- morpholinepropanenitrile ----.

Column 18, line 66
"butoxybenezenamine" should read
---- butoxybenzenamine ----.

UNITED STATES PATENT AND TRADEMARK OFFICE
CERTIFICATE OF CORRECTION

PATENT NO. : 4,920,116

DATED : April 24, 1990

INVENTOR(S) : Thomas K. Morgan, Jr., et al.

It is certified that error appears in the above-identified patent and that said Letters Patent is hereby corrected as shown below:

Column 21, line 48
"N-(1-napthaleny)" should read
---- N-(1-napthalenyl) ----.

Column 23, line 18
"(2-propenyl)amino]ethyl]-[(propylsulfonyl-"
should read
----(2-propenyl)amino]ethyl]-4-[(propylsulfonyl ----.

Signed and Sealed this

Eleventh Day of February, 1992

Attest:

HARRY F. MANBECK, JR.

Attesting Officer

Commissioner of Patents and Trademarks